(12) United States Patent
Paek

(10) Patent No.: US 6,713,303 B2
(45) Date of Patent: Mar. 30, 2004

(54) METHOD FOR THE MASS PROPAGATION OF ADVENTITIOUS ROOTS OF GINSENG, CAMPHOR GINSENG AND WILD GINSENG BY TISSUE CULTURE AND THE IMPROVEMENT OF THEIR SAPONIN CONTENT

(76) Inventor: Kee-Yoeup Paek, #102-903, Hyundai APT, Yongahm-dong, Sangdang-gu, Cheongju-city, 361-763 Choongcheongbuk-do (KR)

( * ) Notice: Subject to any disclaimer, the term of this patent is extended or adjusted under 35 U.S.C. 154(b) by 7 days.

(21) Appl. No.: 09/998,136

(22) Filed: Dec. 3, 2001

(65) Prior Publication Data

US 2002/0142463 A1 Oct. 3, 2002

(30) Foreign Application Priority Data

Jan. 19, 2001 (KR) .......................................... 2001-3284
Jan. 19, 2001 (KR) .......................................... 2001-3285

(51) Int. Cl.$^7$ ................................................. C12N 5/00
(52) U.S. Cl. ....................................................... 435/420
(58) Field of Search ......................................... 435/420

Primary Examiner—Bruce R. Campell
Assistant Examiner—Annette H Para
(74) Attorney, Agent, or Firm—Birch, Stewart, Kolasch & Birch, LLP

(57) ABSTRACT

The present invention relates to a method for mass propagating the adventitious root of ginseng, camphor ginseng, wild ginseng by tissue culture and improving the saponin content. More specially, the method comprises the steps of: tissue culturing of the leaf, root, stems of ginseng, camphor ginseng, wild ginseng and dissecting the callus; Propagating the adventitious root, which was developed by above dissected callus; Mass culturing of the propagated adventitious root in a bioreactor. Especially, the present invention makes it possible to produce the adventitious root that has enriched saponin content and the ratio of diol saponin and triol saponin being the same level of the natural ginseng, thereby, it can provide more valuable adventitious root in commercial and usefulness.

9 Claims, No Drawings

METHOD FOR THE MASS PROPAGATION OF ADVENTITIOUS ROOTS OF GINSENG, CAMPHOR GINSENG AND WILD GINSENG BY TISSUE CULTURE AND THE IMPROVEMENT OF THEIR SAPONIN CONTENT

TECHNICAL FIELD

The present invention relates to the method for mass propagation of adventitious roots of ginseng, camphor ginseng, and wild ginseng by tissue culture and the improvement of their saponin content. More specifically the present invention relates to a method for improvement of saponin content and mass propagation of adventitious roots of ginseng, camphor ginseng, and wild ginseng by tissue culture which can produce in vitro adventitious roots that have excellent commercial value and effectiveness. This product was produced by including adventitious roots from callus, which was formed by tissue culturing of the leaf, root and stem of cultivated ginseng, camphor ginseng, and wild ginseng. After inducing the adventitious roots, it was mass propagated by shaking incubation or bioreactor incubation. In the mass propagation process, the optimal cultivating conditions which the saponin contents in the cultivated ginseng or wild ginseng yields almost the same contents in the natural ginseng were identified.

BACKGROUND ART

Botanically, ginsengs belong in Panax genus of Araliaceae family and their roots are used for medical purposes.

Globally, 6–7 plant species are known to belong to this species. Also, 3 types of the ginsengs are cultivated economically and traded in the ginseng market.

Geographically, ginseng whose plant name is "Panax ginseng C.A. Meyer" is distributed and cultivated at Far East Asia and was used for a tonic medicine, which is traditionally the most important oriental herb medicine in china.

Ginseng has been known to have excellent effects in curing and promoting recovery from diverse diseases and a broad research on ginseng's drug action component and pharmacological effect have been conducted.

Until now, the scientifically proved important major effect is the maintenance of homeostasis of body control function. Based on this function, anti-fatigue and anti-stress effect, anti-diabetes effect, blood pressure control effect, anti-cancer effect, prevention of arteriosclerosis and high blood pressure, brain function fortification, gastrointestinal function reinforcement, immunity reinforcement, anti-virus effect are to be reported.

The primary effective components of ginseng are saponin, sapogenin, polyacetylene, pyragen derivatives, maltol.

However, it has some uneconomical aspects due to the facts that the natural ginseng, which has medical purposes, requires a long-term cultivation at the well drainage and cool highlands for 4–6 years. Also, it will be affected by the natural climate and will not be able to crop continuously, thus appearing uneconomically.

Accordingly, the plant tissue cultivating research has been studied to produce mass propagation of the precious medical ginseng all year around without any impaction of the climate. The method is to produce a ginseng tissue that has as much effective component as the natural medical ginseng by cultivating an indeterminate form of callus, which is obtained by culturing the root of the natural medical ginseng, in various nutrient media under different environmental conditions.

The technology of the mass propagating method of ginseng trichoid root (hairy root) has been registered as a domestic patent under the public patent number of 1993-0000004.

At present, the technology for tissue culturing of Korean ginseng, American ginseng and Tenchi ginseng for multi-purpose is commonly practiced. In particular, the cultivation of callus, which was obtained from culturing various tissues of ginseng, organ differentiation and the successful cell culture of callus, are reported in the professional journals. However these experiments are mainly confined in the analysis of the impacts of the physical and chemical factors on the propagation of callus and cell. But not so many experiments have been reported on the cultivation of adventitious roots of ginseng. The utilization of ginseng requires a lot of effort including a long growing time of 5–6 years or at least 3–4 years and the difficulty of rotating crops. Nevertheless the demand of ginseng is ever growing for the usage in foods, cosmetics and medicine etc.

DISCLOSURE OF INVENTION

The present invention was invented based on the above-mentioned facts. The object of the present invention is to examine closely to the factors that affect the mass propagation of adventitious roots of ginseng, camphor ginseng, and wild ginseng so as to produce the ginseng all year around in the growth controller through the tissue culture of adventitious roots of ginseng, camphor ginseng, and wild ginseng in a shaking incubator or in a bioreactor. In the mean time the present invention is to provide an improved method for increasing saponin content in the adventitious roots of ginseng, camphor ginseng, and wild ginseng compared with the cultivated ginseng and wild ginseng and to induce the level of the saponin composition ratio as same as the natural ginseng by finding the optimal cultivation condition. Therefore, the present invention makes it possible to produce high saponin contented ginseng that has high commercial value and effectiveness.

The other object of the present invention is to apply the present method of mass propagation of the adventitious roots to the high added value products including camphor ginseng, and wild ginseng so as to make it possible to provide and produce raw materials of foods and substitute medicines.

BEST MODE FOR CARRYING OUT THE INVENTION

To achieve the above objects of the present invention, the method for mass propagating the adventitious roots of ginseng, camphor ginseng, and wild ginseng comprises the steps of:

Culturing the tissues of root, stem, leaf from ginseng, camphor ginseng, cultivated ginseng and wild ginseng and desertion callus;

Propagating the developed adventitious root that was deserted from callus; and

Mass culturing the propagated adventitious root in the bioreactor.

The method to improve the saponin content of tissue cultured adventitious root for the mass propagation comprises the steps of:

Preprocessing of the one of adventitious root, obtained from tissue culturing of the ginseng, camphor ginseng, and wild ginseng using a growth regulator;

Seeding the preprocessed adventitious root in the media containing jasmonic acid or methyl jasmonic acid;

Culturing the adventitious root under the light in a balloon shaped or conical shaped bioreactor; and Transferring the adventitious root to nitrogen excluded media within 5–10 days before harvest.

The method for the improvement of saponin content of the tissue cultured adventitious root for the mass propagation is to increase the diol-saponin and the triol-saponin of the adventitious root to the level of those in natural ginseng, thereby providing adventitious roots that have enough commercial value and usefulness in their effects.

Therefore, the present invention makes it possible to produce organic ginseng that are not affected by environments, soils and various contamination by agricultural chemicals all year around in the laboratory or in the factory. Subsequently, this invention makes it possible to satisfy the consumer's desire for consumption by mass propagating the highly recognized wild ginseng in the standardized cultivator.

The primary object of the present invention was to examine closely the factors that affect the propagation of the adventitious root. The secondary object is to cultivate the adventitious root in a bioreactor using the most effective media and to examine the affect of the type of the bioreactor and the amount of the air injection to the bioreactor on the growth rate so as to solve the technical problems associated with the industrialization.

Therefore, the best mode for carrying out the invention consists following contents.

A 2–3 $mm^2$ sized section was obtained from one of the sterilized ginseng, camphor ginseng, and wild ginseng and was seeded on a MS media containing 1.0–10.0 mg/L of 2,4-D (2,4-dichlorophenoxy acetic acid), pichioram, NAA naphthaleneacetic acid) to induce callus. The most desirable effect could be obtained when the concentration of added chemicals was 2.0 mg/L.

After propagating the induced callus in a MS media containing 0.1–5.0 mg/L of 2.4-D as a growth regulator, it was subcultured every 2–4weeks Then, transferred to a MS media containing 1.0–5.0 mg/L of IBA or NAA to produce a adventitious root. Instead of using MS media, SH(Schenk and Hildebrandt) media, B5(Gamborg)media, LP(Quorin and Iepoivre)media and White media were used to propagate callus. But the similar effect was obtained except for the difference depending on the culturing period. Among them MS media and ¾ SH media had the most desirable results. Also, a desirable result could be obtained when 1.0–5.0 mg/L of NAA of IBA was used as a growth regulator that affects callus growth.

The above adventitious root was propagated in MS media (ratio of inorganic matter to solvent is ½ to ¾, pH 5.7–6.0, sugar concentration 3–5%) at the temperature of 18–24° C. The randomly sectioned newly formed lateral root including cultured explants in a size of 1–2 cm was seeded in a buoyant balloon type bioreactor and was cultured in a MS media containing 3% sugar under the conditions of 0.05–0.3 vvm of air injection at 22° C. and pH 6.0 with a growth regulator in an amount of 1.0–10.0 mg/L BSAA (benzo[b] selenienyl acetic acid) or IBA or NAA.

It is desirable to increase the air injection amount in every 2 weeks to prevent the root tangling and to re-seed the adventitious root after 2 weeks of incubation in a bioreactor to prevent rate decrease. It could be possible step by step to mass propagate by scaling up to a 20–50 ton of cultivating adventitious roots using a bigger bioreactor.

EXAMPLES

In this present invention, 6-year-old ginseng, 15-year-old camphor ginseng and over 100-year-old wild ginseng that were cultivated in a field were used for the following experiments.

EXAMPLE 1

Experiment to Set the Optimum Condition for Adventitious Root Propagation

After forming an adventitious root from callus, the following experiments have been conducted to examine the most effective optimum conditions to allow the maximum propagation in a shortest time and to minimize the production cost. After transferring 30 ml of MS media containing 2.0 mg/L of IBA to a disposable petri-dish, 30 adventitious roots sectioned by 10 mm length on the average, which was originated from the wild ginseng callus was seeded.

The propagation speed of the adventitious root was examined under the various experimental conditions of the concentration of the inorganic matter in the media varying 1, ½ and ¾ folds, the pH of the media varying 4.0, 5.0, 5.5, 5.7, 6.0, 6.5, the sugar concentration in the media varying 0%, 1%, 2%, 3%, 4%, 5%, 6%, 7% and the incubation temperature varying 15° C., 18° C., 20° C., 22° C., 24° C., and 26° C.

As a result, the optimum condition for the propagation of the adventitious root was found to be:

The concentration of the inorganic matter ½–¾, pH 5.7–6.0, sugar concentration 3–5% and the incubation temperature 18–24° C.

EXAMPLE 2

The Effect of the Added Growth Regulator on the Adventitious Root

After adding 3% of sugar to the MS media and adjusting pH6.0, basal medium were made by adding 1 mg/L, 2 mg/L, 3 mg/L, 5 mg/L of each of the IBA, NAA and BSAA as auxin. These basal mediums were divided into a 1L flask and a 5L bioreactor.

The roots (average length of 1.0 cm) of the wild ginseng and the cultivated ginseng were seeded in the basal media. The growth increment was observed after 4 week and the results are given in Table 1.

TABLE 1

Effects of the growth regulator on the propagation of the adventitious root.

| Growth regulator (mg/L) | | Cultivated ginseng (Increment rate of biomass) | Wild ginseng (Increment rate of biomass) |
|---|---|---|---|
| | Control | 1.7 | 1.5 |
| IBA | 1 | 4.5 | 4.3 |
| | 2 | 6.7 | 6.8 |
| | 3 | 6.5 | 5.7 |
| | 5 | 3.8 | 4.2 |
| NAA | 1 | 3.2 | 3.4 |
| | 2 | 7.2 | 6.8 |
| | 3 | 6.7 | 6.2 |
| | 5 | 4.2 | 3.8 |
| BSAA | 1 | 5.3 | 5.0 |
| | 2 | 13.2 | 12.5 |
| | 3 | 11.4 | 11.7 |
| | 5 | 4.8 | 3.9 |

As indicated in table 1, media that had not been treated by the growth regulator showed less than 2 times the biomass increment, whereas the media treated by IBA or NAA showed more than 5 times of the biomass increment at a concentration of 2–3 mg/L. Especially, the media treated by BSAA, a newly synthesized auxin, showed a remarkable increment of the biomass under the concentration of 2–3 mg/L, suggesting the most effective concentration of the growth regulator is ef 2–3 mg/L.

The comparison of the cultivated ginseng and the wild ginseng showed not so much difference in the biomass increment and a similar growth pattern in the bioreactor. Therefore, it is desirable to add growth regulators including NAA, IBA and BSAA to mass propagate the adventitious root of the ginseng in the bioreactor.

EXAMPLE 3

The Effect of Seeding Method on the Adventitious Root Propagation

To examine the effects of preparation methods on teh root propagation when culturing the adventitious root of the cultivated ginseng and the wild ginseng in the bioreactor, the following methods were used. The first one is to culture the non-sectioned adventitious root in a MS media containing 2 ml/L of BSAA. The second one is to culture thelateral root only excluding the explants and the last one is to culture the sectioned adventitious root of 1–2 cm length including the explants and lateral root. Table 2 shows the results of each method after 4 week cultivation.

TABLE 2

The effects of subculturing of the adventitious root on the biomass increase (After 4 weeks culture).

| Culturing method | Cultured ginseng | | Wild ginseng | |
| --- | --- | --- | --- | --- |
| | Biomass increment | Drymass increment | Biomass increment | Drymass increment |
| Culturing non-sectioned adventitious root | 1.4 | — | 1.5 | — |
| Culturing the lateral root only | 11.2 | 13.6 | 10.5 | 10.8 |
| Culturing the sectioned adventitious root of 1-2 cm length including the explants and lateral roots | 12.4 | 14.7 | 13.2 | 15.9 |

As shown in table 2, for the case of transplanting the lateral root with the explants to a new media, the lateral root has not been developed and the browning phenomenon has appeared so that the biomass had not been increased. On the other hand, for the case of culturing the sectioned lateral root instead of the originated explants, the biomass and the number of the developed lateral roots were increased. However, it took a long time to seed that it seemed to be not effective. For the case of seeding the newly developed lateral roots that were sectioned randomly in a length of 1–2 cm, including the cultured explants, the rate of multiplication has been increased more than 15 times, indicating that this case was the most effective method for the increase of biomass weight. Therefore, It is desirable to seed the adventitious root having both the explants and the lateral root, which is sectioned in the length of 1–2 cm.

EXAMPLE 4

The Effect of the Bioreactor Shape on the Adventitious Root Propagation

For the case of culturing the adventitious root using the bioreactor for the mass propagation, the effect of the shape of bioreactor on the adventitious root propagation is examined for the following bioreactor shapes. The culturing has been done in a pilot scale of 500L, 1000L of a buoyant balloon shaped bioreactor and the 500L, 1000L of buoyant drum shaped bioreactor for 40 days. The effects of the shape of bioreactor on the biomass increment were compared and the results were given in table 3.

The temperature was adjusted to 22° C., and the amount of air injected into the bioreactor was 0.05–0.3 vvm. 3% sugar added MS media was used and 2.0 mg/L of BSAA was added as a growth regulator and the pH was adjusted to 6.0.

TABLE 3

The effect of the shape of bioreactor on the propagation of adventitious root of the wild ginseng (After 40 days culture).

| The shape of incubator | Scale (L) | Primary seeding amount (kg) | Biomass (kg) | Drymass (kg) |
| --- | --- | --- | --- | --- |
| Buoyant balloon shape | 500 | 2 | 88 | 6.5 |
| | 1000 | 3 | 185 | 12.4 |
| Buoyant drum shape | 500 | 2 | 80 | 5.7 |
| | 1000 | 3 | 174 | 10.8 |

As shown in table 3, generally the buoyant balloon shaped bioreactor was more effective in increasing the biomass and drymass than the drum shaped bioreactor. It is desirable to prevent the root tangle by increasing air injection amount every 2 weeks because the adventitious root tangle occurs as the culturing time becomes longer. It is also desirable to prevent the total production amount decrease, caused by floating phenomenon of the adventitious root after 4 weeks of culturing. Therefore, it is also desirable to re-seed (1 kg) after 2 weeks culturing. It is also desirable to use a 1–3 ton scaled up incubator with a knife in the attached motor so as to cut the newly developed adventitious root in a length of 2–3 cm as in example 3 before using a 50L, 100L scale of a seed incubator or 20–50 ton scale of a incubator.

As shown in earlier, the method for the mass propagation of adventitious root of the ginseng, camphor ginseng and wild ginseng has been proven high productivity of biomass, convenient to handle and have a tendency to increase the drymass. Therefore, it is an innovative method for mass production. Also the present invention made it possible to propagate the adventitious root of cultivated ginseng, camphor ginseng and wild ginseng by tissue culture using the adventitious root propagation method in the MS media, SH media and B5 media. The present invention provides not only the method to increase the saponin content of the harvested adventitious root or the adventitious root under culturing process but also the way to regulate the trio/diol ratio close to the natural ginseng level.

EXAMPLE 5

The Effect of the Bioreactor Shape on the Saponin Content

After seeding the adventitious root, which was sectioned in a length of 1–2 cm in a MS media or SH media containing 3% of sugar, 2.0 mg/of IBA, the flask and a balloon shape, conical shape, bulb shape and drum shape incubator were used to culture the adventitious root. After 4 weeks, the saponin content was increased. The results are given in table 4.

The measurement of saponin content was followed by the standard method for the analysis of ginseng constituent of The Korean Ginseng Research Institute.

TABLE 4

Comparison of saponin content by shape of the culture instrument.

| Shape of culture instrument | Ginsenoside content (mg. 1 g drymass) | | | Ginsenoside productivity (mg.L) |
|---|---|---|---|---|
| | Rg group | Rb group | total content | |
| Balloon shape | 4.62 | 7.72 | 12.34 | 124.63 |
| Conical shape | 4.50 | 7.74 | 12.14 | 110.47 |
| Bulb shape | 3.67 | 5.96 | 9.63 | 61.63 |
| Drum shape | 3.33 | 4.68 | 8.01 | 28.84 |
| Δ-flask | 2.87 | 4.92 | 7.79 | 33.50 |

As shown in table 4, the saponin content was high when cultured in the conical shape bioreactor or the balloon shape bioreactor, but when cultured in the drum shaped or flask the saponins content was low. Therefore, it was desirable to use a balloon shape or conical shape bioreactor when culturing the adventitious root of the ginseng, camphor ginseng and wild ginseng.

EXAMPLE 6

The Effect of Jasmonic Acid and Methyl Jasmonic Acid Treatment on the Saponin Content While culturing the adventitious root of cultivate ginseng, camphor ginseng, wild ginseng in a balloon shape bioreactor, the saponin content in the adventitious root was examined at the initial time, 10 days before harvest, and after harvest with the treatment of various concentrations of jasmonic acid and methyl jasmonic acid.

The experiment was conducted under the conditions of pH 6.0 and the MS media added with 3% sugar and 2.0 mg/L IBA.

The saponin content in the adventitious root was measured for the root treated by various concentrations of jamonic acid or methyl jamonic acid of 0, 1, 2, 5, 10 mg/L 10 days before harvest and the root washed by tap water obtained from the MS media not containing sugar or the treated root by tap water which includes jasmonic acid or methyl jasmonic acid, for one week. The result was given in table 5.

TABLE 5

The effect of jasmonic acid concentration.

| Jasmonic acid Concentration (mg/L) | Ginsenoside content (mg. 1 g drymass) | | | |
|---|---|---|---|---|
| | Rg Group | Rb Group | Total content | Rb/Rg |
| 0 | 3.92 | 7.49 | 11.42 | 1.95 |
| 1 | 2.83 | 13.29 | 16.09 | 4.68 |
| 2 | 4.46 | 24.19 | 28.69 | 5.45 |
| 5 | 4.15 | 34.69 | 38.82 | 8.43 |
| 10 | 5.53 | 54.29 | 59.87 | 9.83 |

As shown in table 5, In the initial culture treated by two materials, the growth increment was inhibited.

The saponin content reached 7–8% for the root treated by the bioreactor for 10 days before harvest or after 7 days for the propagated adventitious root after harvest that was washed by water and then treated by jasmonic acid or methyl jasmonic acid.

This suggests that the saponin content was remarkably increased compared to that of the cultivated ginseng whose saponin content was 2–3%. However he ratio of the diol and triol tended to increase more for the treated ginseng the cultivated ginseng.

Therefore, it is desirable to treat the root with jasmonic acid or methyl jasmonic acid since the jasmonic acid treated root has total saponin content more higher than the non-treated one.

EXAMPLE 7

The Effect of the Nitrogen Elimination in the Media on the Saponin Content

When culturing adventitious root of ginseng in a 5L conical shape bioreactor to increase the saponin content, the MS media containing 2.0 mg/L of IBA and 3% of sugar with a fixed pH value of 6.0 was used.

After culturing 20–30 days to reach the maximum propagation of the adventitious root, the root was transferred to the media that was not contained nitrogen for 5–10 days before harvest and the saponin content of this root was examined. The results were given in table 6.

TABLE 6

The effect of the media not treated by nitrogen before harvest on the saponin content.

| Treated root | Ginsenoside content (mg · 1 g drymass) | | | Remarks |
|---|---|---|---|---|
| | Rg group | Rb group | total | |
| Control | 3.8 | 7.4 | 11.2 | |
| Root not treated by nitrogen | 4.6 | 9.8 | 15.4 | |

As shown in table 6, the saponin content was increased in adventitious root which was cultured in media with nitrogen by optimum concentration and then was transferred to a new media for 5–10 days before harvest.

When transferring the media, nitrogen in the form of nitrate and ammonium should not be added and at this time as shown in example 6, adding jasmonic acid could increase the saponin content more effectively.

EXAMPLE 8

The Effect of Light Sources on Saponin Content

To know the effect of various light sources on the saponin content and the saponin ratio of diol and triol during the incubation period of the adventitious root of the cultivate ginseng, camphor ginseng, wild ginseng, 30 ml of MS media, that had the same condition described in example 1 was transferred to a 100 mL flask and then ginseng adventitious roots, which were sectioned at the length of 1–2 cm were seeded. Subsequently, they were cultured under the dark condition and red light(650 nm), blue light(430 nm), methyl halite and a fluorescent light intensity of 40 umol.m-2.s-1 for 16–24 hours. The cultivating room temperature was adjusted to 22–25° C.

The saponin content was measured after 4 weeks later. The results are given in table 7.

TABLE 7

The effects of light intensity and light source on the saponin content.

| Light source | Biomass increment | Saponin content(mg.g$^{-1}$ DW) | | | Saponin productivity |
|---|---|---|---|---|---|
| | | Rg group | Rb group | total | |
| Dark | 11.41 | 2.8 | 4.5 | | 1.61 |
| fluorescent light | 10.09 | 5.3 | 3.7 | | 0.70 |
| methyl halite | 8.87 | 3.5 | 3.4 | | 0.97 |
| blue light | 11.26 | 3.8 | 3.9 | | 1.03 |
| red light | 11.64 | 3.1 | 4.1 | | 1.32 |
| blue light + red light | 10.09 | 3.4 | 2.9 | | 0.85 |

As shown in table 7, it was desirable to culture under the fluorescence light than the dark condition. It was turned out that the treatment with cytokinins or jasmonic acid was highly effective to improve the quality of the adventitious root before incubating.

As mentioned above, the biomass increment of ginseng, camphor ginseng and wild ginseng by tissue culture was decreased but the saponin content, especially the triol saponin has increased.

Also, when culturing under blue light, the ratio of diol and triol was 1:1, which was close to the ratio of the natural ginseng of 1.03. The red light also showed a similar result.

Therefore, increasing the triol saponin content among total saponin contents, which was one of the difficult problems in culturing the adventitious root of ginseng, had been solved effectively. It was an important factor to culture the adventitious root of ginseng under fluorescence light, red light and blue light to maintain the saponin content close to the level of natural ginseng.

EXAMPLE 9

The Effect of the Growth Regulator Treatment on the Saponin Content and Saponin Ratio Among growth regulators, BA(benzyl adenine) 2iP, zeatin, methyl jasmonic acid, TDZ, kinetin which are included in cytokinin groups was treated 1–10 hours before culturing the root tissue of cultivated ginseng, camphor ginseng, and wild ginseng at the concentration of 1–100 mg/L. Immediate after the pretreatment the saponin and the diol:triol content were compared and analyzed. The results were given in Table 8.

TABLE 8

The effect of the growth regulator treatment before culturing on the saponin components.

| Treatment | saponin content | triol/diol | remarks |
|---|---|---|---|
| No treatment | 1.56 | 2.02 | |
| BA treatment | 1.23 | 1.63 | |
| Methyl jasmonate or jasmonic acid | 6.50 | 2.40 | TDZ, kinetin, 2iP and zeatin show similar results |

As shown in table 8, culturing the adventitious root after pre-treatment increased the saponin content by 5 times and the ratio of triol to diol was about 2.4 that was almost the same value in the natural ginseng. In particular, the treatment with the cytokinin groups gave rise to decrease in the saponin content but the ratio of triol and diol was quite similar to that of the naturally cultivated ginseng. Therefore the method to improve the saponin content as maintaining the triol: diol ratio of the cultured adventitious root to 1:1–1:2 was to examine closely the optimum conditions considering the shape of bioreactor, various kinds of growth regulators and their optimum treatment period, media with or without nitrogen treatment and light sources. The present method was an excellent method being able to culture the adventitious root that had the saponin content exceeding the natural ginseng and the ratio of saponin composition being similar to that of the natural ginseng.

Industrial Applicability

As indicated through the examples, the present invention is to establish the optimum propagation condition including the proper media, pH of the media, sugar concentration, proper culturing temperature, kinds of growth regulators for culturing the adventitious roots of ginseng, camphor ginseng, and wild ginseng in a bioreactor, and to industrialize the production of the adventitious roots in the bioreactor through the simplified method of the adventitious root seeding and finding a proper shape of bioreactor that could boost the productivity and propagation which was not invented yet. The present invention was able to produce high additive value of ginseng, camphor ginseng, and wild ginseng all year around without influence of the climate and environmental conditions, and to produce in vitro adventitious root that has 2–3 times higher saponin content compared with the natural ginseng and the similar ratio of diol and triol saponin to that of the natural ginseng by taking optimum conditions including the nitrogen supply interruption to the adventitious root after maximum growth and the light treatment etc.

What is claimed is:

1. A method for adventitious root mass propagation of ginseng, camphor ginseng or wild ginseng by tissue culture, which comprises the steps of:

inducing a callus by seeding any one of a 2–3 mm$^2$ section of ginseng, camphor ginseng, or wild ginseng in a MS medium containing each of 2,4-D (2,4-dichlorophenoxy acetic acid), pichloram and NAA naphthaleneacetic acid) in an amount of 1.0–10.0 mg/L;

forming an adventitious root by transferring the callus to a MS (MurashigeSkoog) medium containing 1.0–5.0 mg/L of ISA or NAA, after subculturing the induced callus in every 2–4 weeks which was propagated on a MS medium containing 0.1–5.0 mg/L of 2,4-D;

propagating the above adventitious root on MS medium;

seeding the propagated adventitious root in a balloon type airlift bioreactor and culturing the propagated adventitious root in a MS medium containing 3% of sugar and 1.0–10.0 mg/L of BSAA (benzo [b] selenienyl acetic acid) or IBA or NAA as a growth regulator to generate a cultured adventitious root; and mass propagating the cultured adventitious root by scaling up in a 20–50 ton bioreactor as a culture vessel.

2. The method for adventitious root mass propagation of ginseng, camphor ginseng or wild ginseng by tissue culture of claim 1, the method for the mass propagation of adventitious root of ginseng, camphor ginseng or wild ginseng by tissue culture under the conditions wherein the ratio of inorganic matter to solvent is ½ to ¾, pH is 5.7–6.0, a sugar concentration is 3–5% and the temperature is 18–24° C.

3. The method for adventitious root mass propagation of ginseng, camphor ginseng or wild ginseng by tissue culture of claim 1, the method for the mass propagation of the adventitious root of ginseng, camphor ginseng or wild ginseng by culture including the seeding method of the propagated adventitious root to the bioreactor through seeding the adventitious root sectioned randomly at a length of 1–2 cm.

4. The method for adventitious root mass propagation of ginseng, camphor ginseng or wild ginseng by tissue culture as claimed claim 1 or 3, wherein the adventitious root of ginseng, camphor ginseng or wild ginseng by tissue culture is cultured in the bioreactor in which a temperature is 22° C., an air injection rate is 0.05–0.3 vvm and a pH is 6.0.

5. The method for adventitious root mass propagation of ginseng, camphor ginseng or wild ginseng by tissue culture of claim 1, wherein the method for the mass propagation of the adventitious root of ginseng, camphor ginseng or wild ginseng by tissue culture including the further includes a re-seeding step of the adventitious root after 2 weeks culturing.

6. A method for improving saponin content of adventitious root of ginseng, camphor ginseng or wild ginseng, when culturing ginseng, camphor ginseng or wild ginseng using tissue culture, the method comprises the steps of:

pre-treating the adventitious root with any one of the growth regulators BA(benzyl adenine), 2iP, zeatin, methyl jasmonic acid, TDZ, kinetin, or jasmonic acid at a concentration of 1.0–100 mg/L for 1–10 hours;

obtaining the adventitious root by tissue culturing one of the ginseng, camphor ginseng and wild ginseng;

seeding the adventitious root, which was pre-treated with any one of the growth regulators, on MS medium containing 3% of sugar and 0.5–5.0 mg/L of IBA or NAA and incubating it in a bioreactor in which the temperature is 22–25° C. and pH is 6.0 under any one of lights selected from the group consisting of blue light, red light, and fluorescent light; and harvesting the cultured adventitious root that was treated 10 days before harvest with 1.0–10.0 mg/L of jasmonic acid or methyl jasmonic acid in a bioreactor for 7 days.

7. A method of culturing adventitious root of ginseng, camphor ginseng or wild ginseng by tissue, the method for improving the saponin content of adventitious root of ginseng, camphor ginseng or wild ginseng by tissue comprises the steps of:

pre-treating the adventitious root with any one of the growth regulators BA, 2iP, zeatin, methyl jasmonic acid, TDZ, kinetin, or jasmonic acid at a concentration of 1.0–100 mg/L for 1–10 hours;

obtaining the adventitious root by tissue culturing one of the ginseng, camphor ginseng and wild ginseng;

seeding the adventitious root, which was pre-treated with any one of the growth regulators, on MS medium containing 3% of sugar and 0.5–5.0 mg/L of IBA or NAA and incubating it in a bioreactor which the temperature is 22–25° C. and pH 6.0 under any one of the lights such as blue light, red light, fluorescent light; and harvesting the cultured adventitious root washing the cultured adventitious root with tap water and then treating it with 1.0–10.0 mg/L of jasmonic acid or methyl jasmonic acid for 7 days.

8. The method for improving saponin content of adventitious root of ginseng, camphor ginseng or wild ginseng, when culturing ginseng, camphor ginseng, or wild ginseng using tissue culture of claim 6, the method for improving saponin content in the adventitious root of ginseng, camphor ginseng or wild ginseng by tissue culture including choosing any one of a balloon type bioreactor or a conical type airlift bioreactor.

9. The method for improving saponin content of adventitious root of ginseng, camphor ginseng, or wild ginseng, when culturing ginseng, camphor ginseng or wild ginseng using tissue culture of claim 6 or 7, the method for improving saponin content in the adventitious root of ginseng, camphor ginseng, or wild ginseng by tissue culture including transferring to a medium which was not added nitrogen; for 5–10 days before the harvest of cultured adventitious root.

* * * * *